United States Patent
Ahnblad et al.

(10) Patent No.: US 8,652,117 B2
(45) Date of Patent: *Feb. 18, 2014

(54) PHARMACEUTICAL COMPOSITION AND NASAL RINSING DEVICE THEREFOR

(76) Inventors: Peter Ahnblad, Stockholm (SE); Robert Halasz, Nacka (SE); Susanne Ahnblad Lagerqvist, Stockholm (SE)

( * ) Notice: Subject to any disclaimer, the term of this patent is extended or adjusted under 35 U.S.C. 154(b) by 368 days.

This patent is subject to a terminal disclaimer.

(21) Appl. No.: 12/810,212

(22) PCT Filed: Oct. 29, 2008

(86) PCT No.: PCT/US2008/081650
§ 371 (c)(1),
(2), (4) Date: Jun. 23, 2010

(87) PCT Pub. No.: WO2009/058910
PCT Pub. Date: May 7, 2009

(65) Prior Publication Data
US 2010/0298810 A1    Nov. 25, 2010

Related U.S. Application Data

(60) Provisional application No. 60/983,581, filed on Oct. 30, 2007.

(51) Int. Cl.
*A61M 31/00*    (2006.01)

(52) U.S. Cl.
USPC .............................. 604/514; 604/27

(58) Field of Classification Search
USPC ...................... 604/19, 26–27, 514, 522, 187
See application file for complete search history.

(56) References Cited

U.S. PATENT DOCUMENTS

| | | | |
|---|---|---|---|
| 6,540,718 B1 * | 4/2003 | Wennek | 604/94.01 |
| 7,296,566 B2 * | 11/2007 | Alchas | 128/200.14 |
| 2003/0111552 A1 * | 6/2003 | Vedrine et al. | 239/329 |
| 2003/0225394 A1 * | 12/2003 | Ahnblad et al. | 604/514 |
| 2005/0028812 A1 * | 2/2005 | Djupesland | 128/200.21 |

* cited by examiner

*Primary Examiner* — Kevin C Sirmons
*Assistant Examiner* — Deanna K Hall
(74) *Attorney, Agent, or Firm* — Fasth Law Offices; Rolf Fasth

(57) ABSTRACT

Vaccine is administered into a nose. A pharmaceutically-acceptable aqueous saline solution carrier comprising from 0.5% to 1.9% salt is provided in a nasal device. The saline solution is administered into a first nasal cavity to rinse the first nasal cavity. The saline solution is added to the first nasal cavity until the saline solution flows via a posterior nasal aperture into a second nasal cavity. A vaccine is then administered into the first nasal cavity.

6 Claims, 2 Drawing Sheets

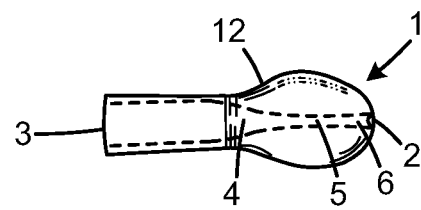
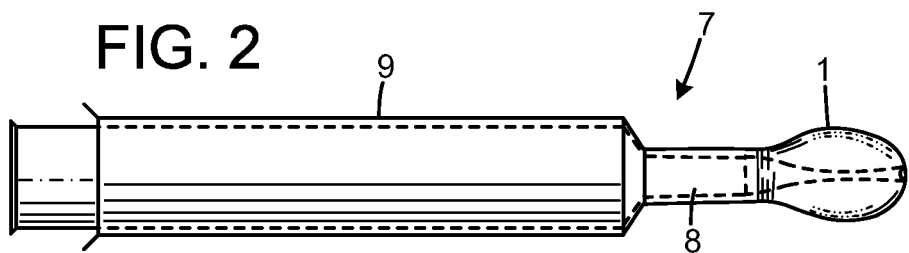
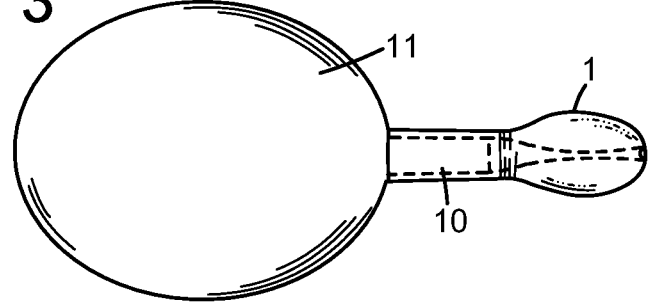
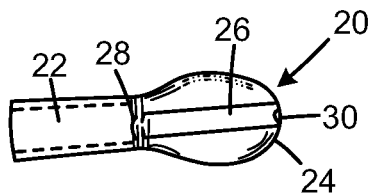

PHARMACEUTICAL COMPOSITION AND NASAL RINSING DEVICE THEREFOR

PRIOR APPLICATION

This application is a U.S. national phase application based on International Application No. PCT/US2008/081650, filed 29 Oct. 2008.

FIELD OF INVENTION

The present invention relates to a pharmaceutical composition for nasal administration and a nasal rinsing device therefor.

BACKGROUND AND SUMMARY OF INVENTION

Rinsing of the nose alleviate and reduce troubles with allergies, infections and troubles after nose surgery since the rinsing flushes away allergens (allergy-forming substance), microbes (virus, bacteria), bi-products of the body (pus, mucus) and dust and soot particles. The inflammatory swelling will be reduced and after nose surgery scabs will be loosened up, whereby the healing process will be accelerated. Rinsing of the nose with salt water is a well-known method and has been recommended by doctors for at least a hundred years.

The known nasal rinsing devices on the market are a potter container for multiple use, which is expensive and has a potter outlet, and two disposable variants which are pre-filled with salt water and water from the Atlantic, respectively, which of course become very expensive to use on regular basis and whose outlet do not function satisfactory and therefore neither their ability to fill up the nose and the fact that they can only be used with the salt water that is pre-filled in the nasal rinsing device.

A first object of the present invention is to provide an outlet-portion for a nasal rinsing device that quickly, comfortably and in a well functioning way may fill the nasal cavity with liquid.

A second object of the present invention is to provide an in-expensive, simple and well functioning nasal rinsing device for multiple-use.

The first object is met by means of an outlet portion for a nasal rinsing device, which is characterised in that it comprises an outlet end, a connection end and nozzle-shaped channel between these ends that show a constriction and an expanded outlet. The outlet portion has the advantage that the liquid which is pressed in through the channel will leave the channel under turbulent flow, whereby the liquid quickly fills out the nasal cavity at the same time as a thin jet is avoided that sprays directly on the mucous membrane of the nasal cavity, which feels unpleasant.

The outlet portion preferably shows a circumference increased portion, for example a droplet or balloon shaped portion, at the outlet end so that the outlet portion seals against the edges of the nostril irrespective of the size of the nostril, which has the advantage that the liquid will not leak out the wrong way and that the shape of the outlet portion will help in opening up the nostril arch, which is the most narrow portion of the nostril.

Preferably, the outlet portion is made of a flexible material that is experienced as soft and comfortable against the nose, such as silicone, soft plastic or rubber.

The shape of the channel at the connection end of the outlet portion is preferably adapted to the connection means of the nasal rinsing device, for example conical with the larges diameter at the end so that the outlet portion fits to a syringe having a conical tip.

The second object is met by means of a nasal rinsing which is characterised in that it comprises an outlet portion of the present invention and a syringe or a compressible balloon for rinsing liquid, whereby the outlet portion is provided at the tip of the syringe or the outlet opening of the balloon, which is provided with connection means. A nasal rinsing device according to any one of the two variants is simple and inexpensive to manufacture and easy to use, especially the syringe variant where it is easy to suck in the rinsing liquid into the syringe before the nasal rinsing, and easy to keep clean, especially the syringe variant.

Of course, the outlet portion may be connected to any other type of nasal rinsing means.

The rinsing liquid may for example be salt water, oil emulsion or salt water provided with a medicine. More particularly, the aromatic composition of the present invention is for nasal administration and has a pharmaceutically-acceptable aqueous saline solution carrier combined with sesame oil and essential oil such as peppermint oil and/or eucalyptus oil. The composition is withdrawn into a syringe and an output portion is sealingly applied to the nostril before the composition is injected.

Another significant problem is to effectively vaccinate against many complicated diseases. Syringes are often used to inject substances below the skin or into muscles. Some patients avoid taking vaccinations because this injection method usually is uncomfortable or even painful. Additionally, vaccines administrated with injections do not give a broader immunity against more complicated genetically diversified strains of viruses such as HIV and influenza virus type A, where there is a need for a broad immunity (cross-immunity) for a successful vaccination. There is therefore a crucial need for a more effective vaccination method.

The nose not only is used for smelling but also for filtering, moisturizing and warming the air that is breathed in before it reaches the lungs. The mucous in the nose has a surface of about 180 square centimeters that is filled with hair cells that transport away particles and other substances towards the throat. During infection and inflammations the effectiveness of this process is dramatically reduced.

The present invention provides a solution to the above-mentioned vaccination problem. More particularly, the method is for administering vaccine into a nose. A pharmaceutically-acceptable aqueous saline solution carrier comprising from 0.5% to 1.9% salt is provided in a nasal device. The saline solution is administered into a first nasal cavity to rinse the first nasal cavity. The saline solution is added to the first nasal cavity until the saline solution flows via a posterior nasal aperture into a second nasal cavity. A vaccine is then administered into the first nasal cavity.

BRIEF DESCRIPTION OF DRAWINGS

The present invention will now be described by exemplifying embodiments of the present invention together with appended drawings, in which:

FIG. 1 illustrates an embodiment of an outlet portion according to the present invention of a nasal rinsing device;

FIG. 2 illustrates a first embodiment of a nasal rinsing device of syringe type according to the present invention;

FIG. 3 illustrates a second embodiment of a nasal rinsing device of balloon type according to the present invention;

FIG. 4 illustrates a third embodiment of a nasal rinsing device according to the present invention;

DETAILED DESCRIPTION

Figure 5:
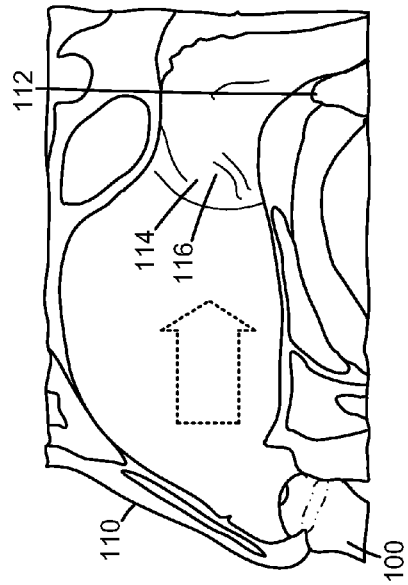
FIG. 5 is a cross-sectional view of a nose.

In FIG. 1 an outlet portion 1 is shown, which comprises an outlet end 2 and a connection end 3. Between these ends 2, 3 a channel 4 is arranged. The channel 4 is nozzle shaped and shows a restriction 5 in the cross section and an expanded outlet 6. At the connection end 3 the channel 4 has a shape that is adapted to the type of connection of the nasal rinsing device at which the outlet portion shall be arranged. In the shown case the channel 4 is conically shaped with the largest diameter in the connection end to fit a syringe with a conically tapering tip, for example a monoject syringe.

The outlet portion 1 has an outer shape that reminds of a lolly where the connection end 3 is the stick and the outlet end 2 is the lolly head. The outlet end 2 shows a circumference enlargement portion 12 that preferably is balloon or droplet shaped, whereby the outer diameter of the outlet portion increases from the outlet end 2 a distance inwards from this where after the outer diameter decreases. This results in the fact that the outlet portion 1 may be put into the nostril a short distance at the same time as the increasing diameter results in that the opening of the nostril fully is filled up by the outlet portion 1 so that it seals between the outlet portion 1 and the nostril. This design also results in that the outlet portion 1 suits all different sizes of nostrils. Preferably the outlet portion 1 is made of a silicone rubber.

When rinsing liquid is pressed into the outlet portion 1 from for example a syringe into the channel 4 the pressure will increase when the liquid passes the restriction 5 and will thereafter increase in velocity when the liquid reaches in the expanded outlet, whereby the flow will become turbulent.

In FIG. 2 a nasal rinsing device 7 according to a first embodiment of the present invention is shown. It comprises an outlet portion 1 provided at the tip 8 of a syringe 9, in the shown case the syringe is provided with a conically-shaped tip 8.

In FIG. 3 a nasal rinsing device according to a second embodiment of the present invention is shown. It comprises an outlet portion 1 provided at a hollow tip 10 at a balloon shaped body 11. The balloon shaped body 11, is compressible to be able to press out liquid comprised within the balloon shaped body 11 through the hollow tip 10 and out through the outlet portion.

When the outlet portion is used, a lukewarm to body temperature warm rinsing liquid is drawn into the syringe 9 or the balloon 11 through negative pressure, whereby it is pressed out through the outlet portion 1 and further into the nostril of the user.

With reference to FIG. 4, a silicone outlet portion 20 of a third embodiment of the present invention has a hollow connection end 22 and an enlarged balloon-shaped outer end 24. The outer end 24 has a channel 26 defined therein that extends from an end section 28 of the of the connection end 22 to an outer tip 30 of the outer end 24. Preferably, the channel 24 has straight inner walls so that the channel 24 either has a constant inner diameter or a constant reduction or increase in diameter. Of course, the channel 26 may also have a variable diameter, if desired. The channel 26 extends from the tip 30 to the end section 28 so that the tip 30 is in fluid communication with the inside of the hollow connection end 22. As described above, the outer end 20 may be connected to a suitable syringe device such as the syringe 9, shown in FIG. 2, so that a suitable composition may be injected into one of the user's nostrils. Once the composition has been withdrawn into the syringe 9, the silicone portion 20 is sealed against the inside of the nostril or the bottom part of the nose and the solution containing the composition is injected with the syringe. Preferably, the portion 20 picks up some air so that the injection is turbulent and not merely linear.

Preferred pharmaceutical compositions of the present invention contain many essential components for nasal administration. The compositions contain a therapeutically effective amount of selected active aromatic agents. The preferred composition contains salt, sesame oil and essential oil such as peppermint oil or eucalyptus oil. The composition may be dissolved in water or another suitable liquid. More particularly, the pharmaceutical composition comprises a finely pulverized salt, such as sodium chloride (NaCl) or any other suitable salt that together with a liquid, such as water, function as a pharmaceutically acceptable aqueous saline solution carrier. The saline solution carrier is physiologically compatible with the human body. The compatibility is important for the user's comfort and to prevent damage of the nasal mucosa or mucous membrane inside the nostrils. The aqueous saline solution carrier may range from 0.1% to about 99.4% weight percent. The salt is present in the solution at a level of about 0.5% to about 1.9%. More preferably, the salt amount is between 0.8% and 1.0% and most preferably about 0.9% weight percent that is very close to the salt level of the human body.

The first essential component of the present invention is sesame oil or any other suitable lubricating oil substances. The sesame oil could be cold pressed oil that contains vitamin E that is a known antioxidant. Antioxidants may be used to discard undesirable substances that are produced by the body. The antioxidants may be useful to neutralize free radical $O_2$ negative molecules that may exist in the body so that the oxygen becomes neutral. The sesame oil also contains a large amount of triglycerides such as lino-acid that are naturally included in the outer parts of the cells of the mucous membrane. The sesame oil may also be used to lubricate the mucous membrane and to prevent any undesirable dryness of the mucous membrane. The rinsing of the nose with just conventional salt solutions has a tendency to dry out the mucous membrane. The first sesame oil component comprises from about 0.02% to about 0.10%, preferably from about 0.03% to about 0.07% and most preferably 0.05 weight percent. If too much of the first component is added, it may be difficult to dissolve the first component in the water. If not enough of the first component is used then the antiseptic and decongestant function of the first component may be lost.

The second component of the present invention comprises an aromatic antiseptic component that has a cleaning effect and prevents excessive growth or development of harmful bacteria. The second component is a decongestant of dried mucous and reduces swelling. The component could be an essential volatile oil such as peppermint oil and/or eucalyptus oil. The second component comprises from 0.003% to about 0.040% of the composition. More particularly, if the second component is peppermint, the component comprises from about 0.005% to about 0.040%, preferably from about 0.012% to about 0.020% and most preferably about 0.016 weight percent. If the second component is eucalyptus, the component comprises from about 0.003% to about 0.020%, preferably from about 0.006% to about 0.010% and most preferably 0.008 weight percent. If too much of the second component is used, the user may experience the solution as being too strong.

The composition of the present invention may be provided in pulverized, tablet or any other suitable form. The examples described below are further embodiments that are within the scope of the present invention. The examples are given solely for the purpose of illustration and are not to be construed as limitations of the present invention, as many variations thereof are possible without departing from the spirit and scope of the invention.

Example 1

A nasal composition is prepared by combining the following components:

| Ingredient | W/W % |
|---|---|
| Sodium chloride | 0.90% |
| Sesame oil | 0.05% |
| *Eucalyptus* oil | 0.008% |
| Water | 100.00% |

A tablet or a suitable amount of a pulverized substance is added to a glass of water and allowed to dissolve in the water. A suitable amount of mixing is preferred to make sure the composition is fully dissolved in the water. The dissolved composition is injected into a nostril with the nasal rinsing device.

Example 2

A nasal composition is prepared by combining the following components:

| Ingredient | W/W % |
|---|---|
| Sodium chloride | 0.9% |
| Sesame oil | 0.05% |
| Peppermint oil | 0.016% |
| Water | 100.0% |

The composition is dissolved in water prior to injecting the dissolved composition into a nostril with the nasal rinsing device.

Figure 6:
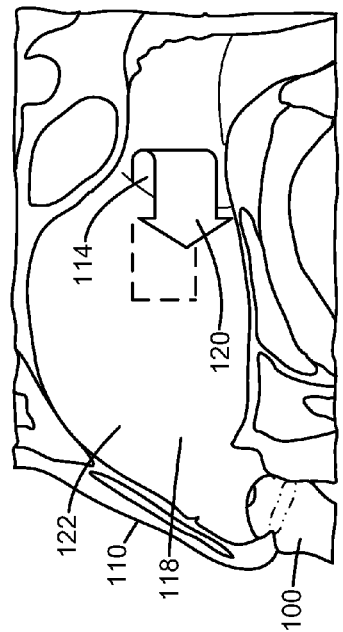
FIG. 6 is a cross-sectional view of the nose showing the posterior nasal aperture extending between the first nostril and the second nostril.
Figure 7:
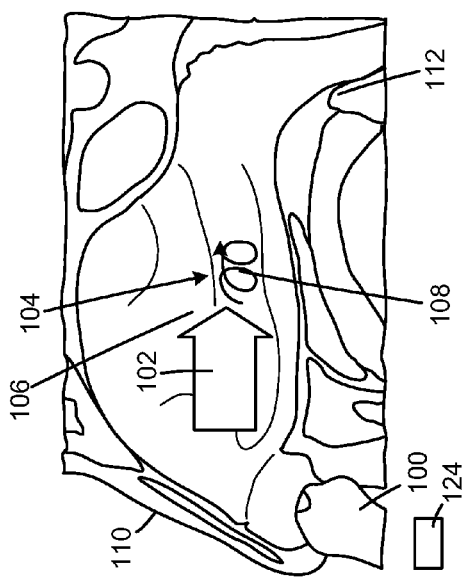
FIG. 7 is a cross-sectional view of the nose showing the liquid flowing from the first nostril through the posterior nasal aperture to the second nostril.

A vaccine substance may also be administered into the nose, as shown in FIGS. 5-7. This is in contrast to the conventional use of syringes to inject vaccine below the skin or into a muscle which can be painful and uncomfortable for the patient. It has been found that the mucous in the nose has cells that react very effectively to locally administered vaccines and thus trigger the immune system of the patient to about or almost 100%. When vaccine is injected by conventional syringes only about 10% of the immune system is effectively used. This means the amount of vaccine that is required when added to the nose may be much less compared to vaccine injected below the skin with a syringe.

The inside of the nose contains antibodies. Anti-bodies are special proteins that the body forms to discover and identify foreign substances such as viruses and bacteria. They are often a deciding factor for the immune system to localize and eliminate foreign substances that may be contagious. The level of anti-bodies may be used to measure the effectiveness and the body's response to the vaccine. It has been discovered that certain anti-bodies, such as SIgA, are only formed after vaccination of the mucous and then only secreted to the mucous. Since the mucous in various parts of the body are similar, nasal vaccination creates not only SIgA antibodies in the nose but also in the vagina and other mucous containing parts. Nasal vaccination may also provide cross protection so that protection against other strains of a virus may be obtained. This is very important for viruses that require vaccine that protects from many different strains such as for example HIV and influenza type A viruses. This cross protection cannot normally be provided by conventionally injected vaccine.

According to the nasal device of the present invention the user may determine a flow of the rinsing liquid or vaccine into a first nasal cavity of a nose. A spiral flow of the liquid and/or vaccine created by the nasal device is soothing and the entire nasal cavity is rinsed. The volume administered is optimized so that the reflex of closing the soft palatine is used so that the vaccine does not flow down into the throat but flows from the first nostril via a posterior nasal aperture or choana, at the nasopharynx or nasal pharynx that extends into the other or second nasal cavity. The arrow shows the flow through the aperture from the first nasal cavity to the second cavity.

Preferably, the nose is first rinsed with the salt solution described above using the nasal device of the present invention before nasal vaccination to improve the effect of the vaccine. The nasal device may also be used to administer the vaccine into the nose. The mucous membrane in the nose normally includes large amounts of different bacteria and waste products that strongly interfere with the immune defense of the mucous membrane. By first rinsing out the nose to substantially remove such bacteria and waste products, the mucous membrane may completely focus on reacting with the later administered vaccine instead which increases the effect of the vaccine. The rinsing is usually effective for up to four hours before the vaccine should be administered to maintain the high effectiveness. The rinsing also enables patients with defective mucous membranes in the nose to effectively react with the liquid vaccine.

If the nasal vaccine includes adjutant substances that may create an inflammatory reaction this increases the risk of side effects of the vaccine. Normally adjutants, that create irritations, are added to the vaccine to trigger the immune system. However, the triggering of the immune system may trigger too much of an inflammatory reaction. It is therefore desirable to keep the amount of added adjutants as small as possible to reduce side effects. The nose rinsing not only reduces the amount of vaccine required but also reduces the need for using adjutants since the rinsing process functions as an adjutant in itself without risking the triggering of too strong of an inflammatory reaction.

The vaccine that is administered into the nose may include potentially illness generating substances such as viruses, bacteria and parasites that are combined with carriers that enhance or otherwise improve the effect of the vaccine.

The vaccine may be administered to the mucous membrane in the nose by drops, spray, inhalers or rinsing. As indicated above, the pre-vaccination rinsing should be carried out immediately before or less than four hours before the administering of the vaccine. The nasal vaccination may also be performed in connection with the nasal rinsing by adding the vaccine directly to the rinsing fluid.

An important feature by requiring all patients to perform the nasal rinsing prior to the application of the nasal vaccine is that the nasal environment is normalized so that individual differences regarding bacteria, pH and other such factors are reduced so that the salt water layer in the nose is similar between all patients. As indicated above, because the nose has been pre-rinsed so the nose is clean from waste products, bacteria et cetera there is less need to use large amounts of adjutants or irritants to break through the immune system in the nose. Because the nasal environment has been normalized there is less need to vary the amount of added adjutants to the individual nose environments.

In operation, a pharmaceutically acceptable or physiological saline solution 104, as described above, is administered into the first nostril to fill the first nasal cavity 106 by using a nasal device 100 that creates a flow 102. It is important to rinse the entire nasal cavity 106 to completely remove particles that may interact with the vaccine and to normalize the mucous membrane regarding such factors as pH value and salt concentration. The waste particles may also affect the immune system and by removing the particles the immune system is ready to react with the vaccine. The pressure built up by the nasal device and the volume of the saline solution is optimized by the nasal device. The rinsing should not be too fast so that there is time for the soft palatine 112 to close. For example, the rinsing should take about 5-7 seconds. If the filling is too slow and the pressure is too low the saline solution may flow along the bottom of the nose and into the second nasal cavity 118 before the first nasal cavity 106 is completely filled. It is therefore important to completely fill the first nasal cavity 106 before any rinsing saline solution 104 may flow, according to the arrow 120 into the second nasal cavity 118 via a posterior nasal aperture or choana 114 that extends between the two cavities 106, 118 that are separated by a nasal wall 122.

Preferably, the saline solution is injected into the first nasal cavity 106 so that it follows a swirling or rotating motion as shown by the arrow 108. The nasal device preferably has a soft "hour-glass" shaped insertion piece that the saline solution changes from a straight/laminar flow to a turbulent flow in the nasal device. The turbulent flow 108 prevents a direct flow or impact on the upper part of the nasal mucous which may damage the mucous membrane is uncomfortable to the patient. Preferably, physiological saline solution 104 should be used that has a salt concentration that is about the same as the salt solution of the body. It may be possible to use a hyper-tone saline solution that has a salt concentration that is slightly higher than the salt solution of the body in order to withdraw liquid from the mucous.

The second nasal cavity 118 is then rinsed in the same way before the vaccine 124 is applied. Upon complete rinsing, the vaccine may then be applied by for example spraying the vaccine into the nostrils. The vaccine may also be in drop or powder form.

While the present invention has been described in accordance with preferred compositions and embodiments, it is to be understood that certain substitutions and alterations may be made thereto without departing from the spirit and scope of the following claims.

The invention claimed is:

1. A method for administering vaccine, comprising:
providing a pharmaceutically-acceptable aqueous saline solution carrier comprising from 0.5% to 1.9% salt and vaccine in a nasal device disposed in a syringe;
connecting an outlet portion of the nasal device to the syringe, the outlet portion having an hour-glass-shaped outlet end;
inserting the outlet portion into a nostril so that the nostril seals around the hour-glass-shaped outlet end of the outlet portion;
building up a pressure of the saline solution and the vaccine in the syringe;
creating a turbulent flow of the saline solution and the vaccine in the hour-glass-shaped outlet end of the nasal device;
injecting the saline solution and the vaccine under the pressure into a first nasal cavity of the nostril with the syringe via the outlet portion;
creating a swirling flow of the saline solution and the vaccine in the first nasal cavity and vaccinating mucous in the first nasal cavity; and
completely filling the first nasal cavity with the saline solution and the vaccine before a soft palatine closes and then transferring the saline solution and the vaccine via a posterior nasal aperture into a second nasal cavity.

2. The method according to claim 1 wherein the method further comprises spraying the vaccine into the first nasal cavity and the second nasal cavity.

3. The method according to claim 1 wherein the method further comprises adding the vaccine to the solution prior to injecting the solution into the first nasal cavity.

4. The method according to claim 1 wherein the method further comprises providing cross-protection by vaccinating mucous with the vaccine.

5. The method according to claim 1 wherein the method further comprises administering the vaccine into the second nasal cavity.

6. The method according to claim 1 wherein the method further comprises the outlet portion having a channel defined therein and adding the saline solution via the channel that has a restriction segment to speed up a flow of the saline solution flowing therethrough.

* * * * *